United States Patent [19]

Boenisch

[11] Patent Number: 4,960,224

[45] Date of Patent: Oct. 2, 1990

[54] CLOSURE AND CONTAINER FOR REGENT AND SLIDES

[76] Inventor: Thomas Boenisch, 5073 San Rodrigo Ave., Santa Barbara, Calif. 93111

[21] Appl. No.: 328,538

[22] Filed: Mar. 24, 1989

[51] Int. Cl.$^5$ .......................... B65D 85/48; B05C 3/00
[52] U.S. Cl. .................................... 206/456; 118/428; 118/429; 220/532; 220/663
[58] Field of Search .......................... 220/20, 20.5, 21; 206/205, 456, 569; 118/407, 408, 428, 429

[56] References Cited

U.S. PATENT DOCUMENTS 3,822,780  7/1974  Ulmer et al. .................... 206/205 X
4,635,791  1/1987  Jackson et al. ................. 206/456 X Primary Examiner—Stephen Marcus
Assistant Examiner—Nova Stucker
Attorney, Agent, or Firm—Plante Strauss Vanderburgh and Connors

[57] ABSTRACT

A tissue staining cassette includes a container for reagent, a slide retainer for securing a plurality of slides and for suspending the slides in reagent in the container with tissue specimens immersed in the reagent. The slide retainer consists of an open ended cylindrical body having channel containing inserts disposed in the body with the channels opposed for receiving the edges of slides. Depending spring arms corresponding to each of the channels are affixed in the cylindrical body and the end of each spring arm extends into its respective channel. As slides are inserted into the channels the spring arm is displaced and responsive to the displacement the slide is clamped between the end of the spring arm and a wall of the channel. In another embodiment resilient wall members extend across the bore of the slide retainer body to divide the bore of the retainer body into slide receiving areas corresponding to the opposed channels.

The kit includes a sealed reagent filled container for each step of the staining operation, at least one slide retainer and a cover for each reagent container for storing the container when not in use after the liquid tight seal has been removed.

9 Claims, 5 Drawing Sheets

CLOSURE AND CONTAINER FOR REGENT AND SLIDES

FIELD OF INVENTION

This invention relates to apparatus for handling and storing reagents and sample containing slides and more particularly to a cassette for both transporting and storing reagents and for manipulating specimen slides during the staining thereof and a reagent kit.

BACKGROUND OF THE INVENTION

For the microscopic examination of the tissue sections and other biological and botanical material, it is usually necessary to chemically treat sections of the material so that its structure can be observed under a microscope. This procedure is referred to as staining. Traditionally, a thin section of tissue or other biological material to be examined is mounted on a transparent slide which is retained on a horizontal surface, such as a laboratory workbench. The mounted section is then treated sequentially to a series of reagents which culminates in the specific staining of structural or composite features of the specimen. The choice of the reagents and the sequence in which they are applied to the specimen sections depends upon the nature of the specimen being examined and the particular features to be examined. Employing conventional staining techniques, a specimen is placed on a glass slide and a drop of the particular reagent being employed in the staining operation is placed on the specimen. Following a given contact period, the specimen is washed with distilled water or a buffered saline solution or the like to wash the reagent away and if required a drop of a second reagent placed on the specimen to continue or complete the staining procedure. Such manual methods do not always lend themselves readily to the processing of a large number of specimens by a single operator. For example, developments in the reagents employed has in many cases significantly reduced incubation times from a matter of days or hours to a matter of minutes. Consequently, it is very difficult for a single operator to stagger specimens reproducibly through the staining procedure and, consequently, an operator is only able to process a few specimens at a time.

Automation and batch staining techniques have been developed to improve the processing rate and increase the number of specimens which can be processed reproducibly by an operator. Automated techniques and devices, such as for example the "CODE-ON SLIDE STAINER" distributed by Fischer Scientific allow for automated processing and staining of many tissue sections. However, these devices are very costly and are normally available only to large institutional and commercial laboratories. Batch staining, on the other hand, markedly reduces the labor involved and also improves consistency and sensitivity. However, batch staining techniques presently involve the use of relatively large reagent volumes and incubation times of up to four days so that batch staining procedures are unpopular and normally impractical.

SUMMARY OF THE INVENTION

Accordingly, it is an object of the present invention to provide an economical and efficient system for reproducibly staining a plurality of specimen sections mounted on slides.

Another object of the present invention is to provide a single cassette which serves both as a container for shipping and storing reagents and as apparatus for staining slide mounted specimens.

Yet another object of the present invention is to provide a re-useable system for batch staining tissue slides and for storing reagent.

Yet another object of the invention is to provide a kit which includes reagent and apparatus for batch staining a plurality of sample containing slides.

These and other advantages of the present invention are achieved by a cassette comprising a container for reagent and for incubating specimens, a lid for closing the container and storing the container and reagent when not in use, and a slide retainer which is adapted to retain a plurality of slides for suspension in the reagent of the container during the staining operation and for manipulating the slides during the staining procedure. In accordance with the invention, the reagent can be utilized to stain a plurality of slide batches without significant loss of reagent and without wasting reagent. In addition, the slide retainer of the present invention permits easy transfer of a plurality of slides being batch stained between reagent containers and/or washing steps.

In a preferred form of the invention, the cassette is provided as part of a kit which may include one or more containers which are filled with the particular reagents for a given staining procedure and which are provided with a liquid-tight seal for shipping. The kit further includes a lid for each of the containers for storing reagent when the liquid-tight seal has been removed and one or more slide retainers for slide handling. The reagent is provided in the proper quantity to ensure total immersion of the specimens when suspended in the container and the reagent is provided in the proper concentration for immediate use by the operator. The components of the kit are provided in a suitable shipping container.

BRIEF DESCRIPTION OF THE DRAWINGS

The invention will be more clearly understood from the following detailed description taken in connection with the drawings in which.

DETAILED DESCRIPTION OF THE INVENTION

Figure 1:
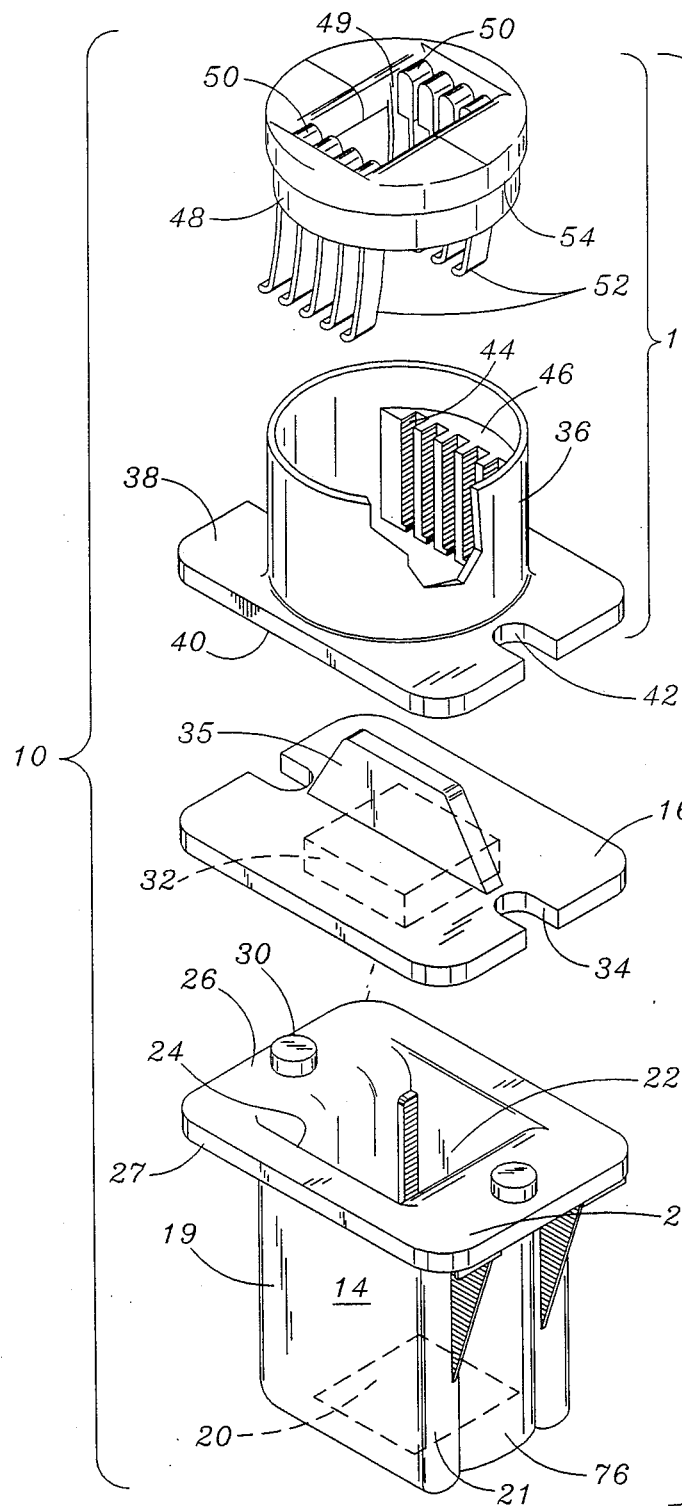
FIG. 1 is an exploded prospective view of a cassette of the present invention, partially broken away for purposes of illustration.
Figure 2:
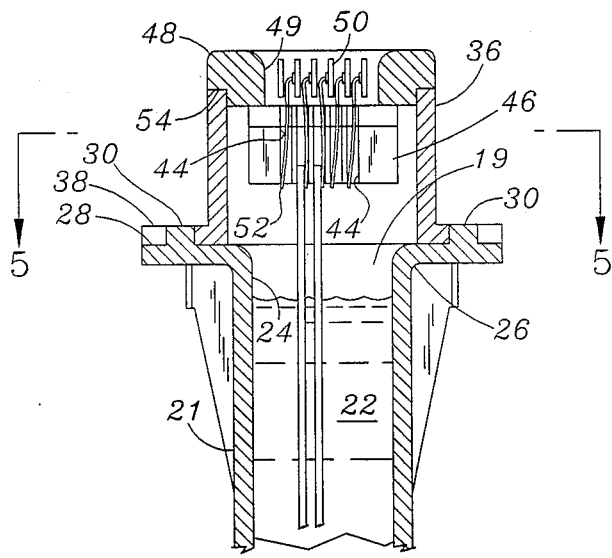
FIG. 2 is a side sectional view in enlarged scale and partially broken away for compactness of illustration of the slide retainer of FIG. 1 in position on the container during a staining operation.
Figure 3:
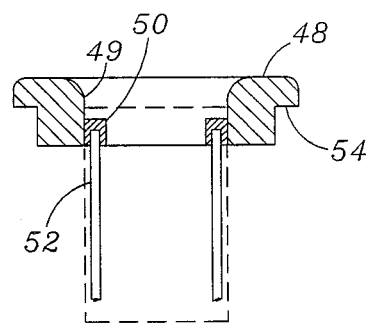
FIG. 3 is an end sectional view of the slide retainer of FIG. 2.
Figure 4:
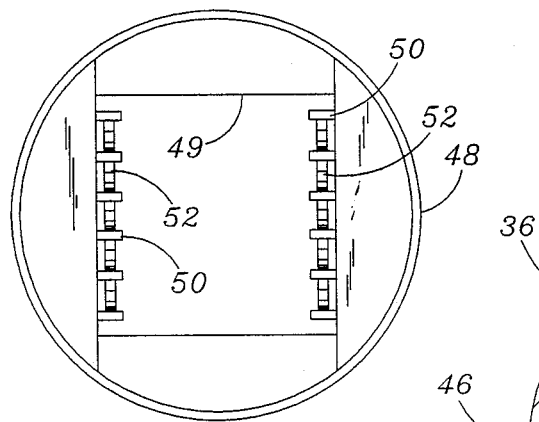
FIG. 4 is a top plan view of the slide retainer illustrated in FIG. 2.
Figure 5:
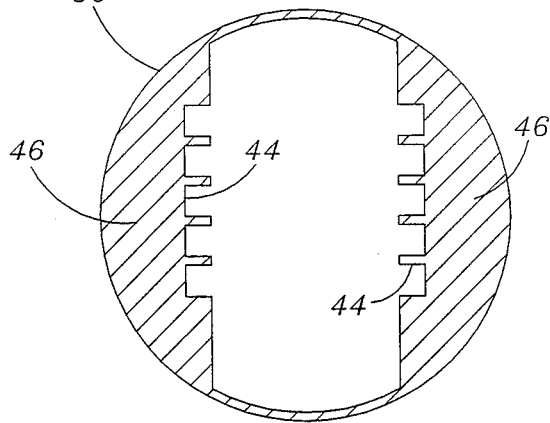
FIG. 5 is a top sectional view of the slide retainer illustrated in FIG. 2 taken through line 5—5 of FIG. 2.
Figure 6:
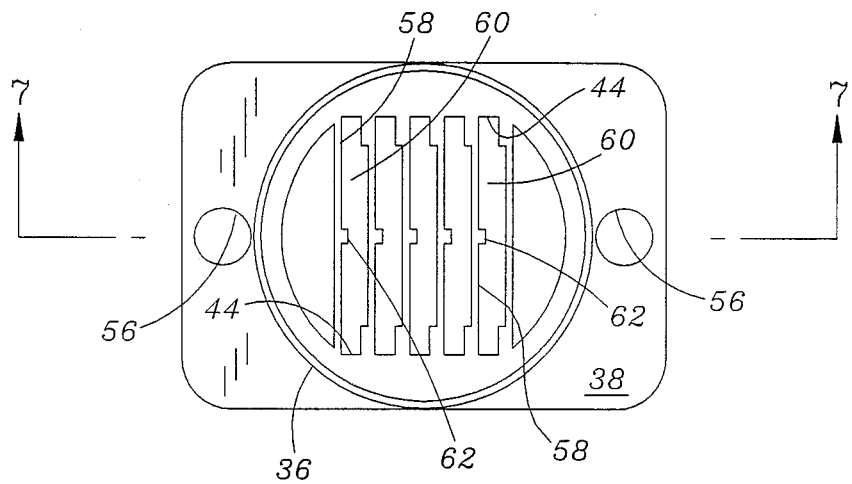
FIG. 6 is a top plan view of another embodiment of a slide in accordance with the present invention.
Figure 7:
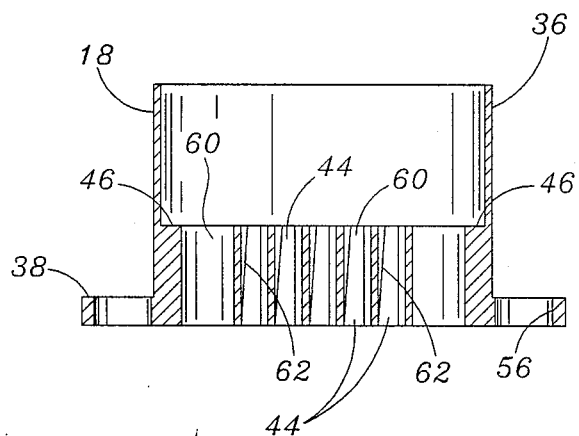
FIG. 7 is a side sectional view of the slide retainer of FIG. 6 taken along line 7—7 of FIG. 6.

Referring now to the drawings, FIG. 1 illustrates a cassette constructed in accordance with the present invention and which comprises a container 14, a lid 16 and a slide retainer, shown generally as 18. The container is a hollow body defining a bottom wall 20, a top wall 26, side walls 19 and end walls 21 which define an interior 22. A mouth 24 is provided in the top wall 28 for communication with container interior 22. The top wall 26 is extended outwardly from the walls 19 and 21 to define a flange 27, the upper surface 28 of which serves as a support surface for the cover 16 and slide retainer 18 as will be described hereinafter. The upper surface 28 is provided with a pair of guide projections 30 which cooperate with corresponding means on the cover 16 and the slide retainer 18 to ensure proper positioning of either of these components when in position over the mouth 24 of the container 14. At least the end walls 21 of the container 14 are transparent, for viewing objects in the container and preferably each of the end walls is formed with a convex portion 76 which serves to magnify objects in the interior 22 of the container.

Figure 8:
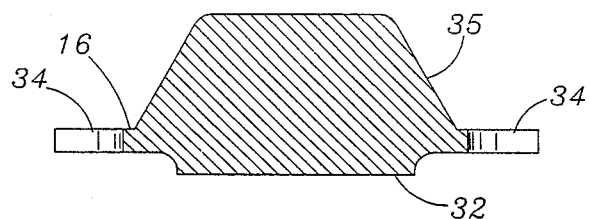
FIG. 8 is a side sectional view of the cover of FIG. 1.

The cover 16 (FIGS. 1 and 8) has essentially the same plan configuration as the periphery of the top wall 26 of the container 14 and is provided with an inwardly extending center portion 32 which is adapted to fit into the mouth 24 to seal the interior 22 of the container when the cover is in position. The cover 16 is also provided with a cut-out portion 34 which corresponds in size and position to the projections 30 on the surface 28 of the top wall 26 and which cooperate with the projections to locate and retain the cover over the mouth 24 of the container. A handle 35 is provided on the upper surface for easier manipulation of the lid 16.

The slide retainer 18, as illustrated in FIGS. 1–5, consists of an open-ended cylindrical body 36, the lower edge of which is extended radially outwardly to define a flange 38 having a planer lower surface 40 adapted to be supported by the surface 28 of the container when the slide retainer is positioned over the mouth 24 of the container. The flange 38 is provided with cut-outs 42 which correspond to the position of the projections 30 and which serve to guide and retain the slide retainer over the mouth 24 of the container 14. An opposed pair of channel members 46 are affixed within the cylindrical body 36 and are provided with facing, essentially planer surfaces in which are disposed a plurality of channels 44. The channels open at the top, bottom and facing surfaces of each of the members 46 and are aligned with their respective opposing channels for the insertion of the edges of pairs of slides in each of the channels 44. An annular insert 48 having a center opening 49, which is configured to match the configuration of the mouth 24 of the container 14, carries depending spring arms 52 by means of inwardly extending fingers 50 affixed to opposing edges of the opening 49. Each of the spring arms 52 corresponds to a channel 44 and is received therein. The depending end of each spring arm 52 is disposed in a respective channel 44 and asserts a clamping action for retaining slides in the channel 44. Preferably, the upper end of the insert 48 is extended outward to define a shoulder 54 which rests on the top rim of the cylindrical body 36 and which serves as a stop to prevent over-insertion of the insert 48 and possible damage to the interior of the cylindrical body 36.

In practice the cassette and reagents are preferably provided in the form of a kit which includes one or more containers 14 in which is disposed such reagents as may be required for a particular staining operation. Since the kits are provided for batch staining operations and for a plurality of staining operations, the reagents are provided in sufficient quantity to ensure that the specimens are fully immersed in reagent when disposed in the container 14 and the concentration is somewhat higher, on the order of 10 to 20% to allow for some loss of reagent volume and potency due to reagent loss that may occur as a result of reagent being carried out on the slides and specimens when they are removed from the container. The container 14 is provided with a suitable liquid tight seal, such as for example an aluminum foil seal or a similar plastic seal so that the reagent is not lost during shipping. One or more slide retainers 18 and covers 16, corresponding in number to the containers 14 in the kit, are provided. The kit is packed in a suitable container for shipping and storage until ready for use.

To conduct batch staining using the cassette illustrated in FIGS. 1–5, pairs of slides are inserted end wise in the slide retainer 18 through the opening 49 so that the longitudinal edges of the slides are disposed in an opposed pair of channels 44 and the slide pair is clamped in its respective channels 44 by the action of the spring arms 52 acting against the edges of the slide. The slide pairs are positioned back-to-back so that the specimens face outwardly for exposure to the reagent in the interior 22 of the container 14 and as will be noted in a preferred embodiment, the center portion of the slide retainer is open so that there is no interference or disturbance of the specimens on the slides.

Upon completion of the incubation step, the slide retainer 18 is removed from the container 14 and transferred to the next staining operation or washing step as the case may be. If no further staining is to be carried out the cover 16 is positioned over the mouth 24 of the container 14 and the container put away for storage until needed.

As illustrated, the slide retainer is adapted with five channels 44 so that it can handle up to five slide pairs or ten individual specimens per batch operation. The container 14 is configured to hold approximately 11 ml. of the reagent which ensures, when five slide pairs are inserted in the container, that there is sufficient displacement of reagent to more than cover the specimens on the slides for multiple batch staining operations. It will be understood, however, that the cassette can be configured a greater or a lesser number of slides in which case the size of the container 14, and the quantity of reagent will be adjusted accordingly.

Although the material of construction of the cassette is not critical, it is highly preferred that at least the end walls 21 of the container be transparent so that the specimens can be viewed while in the container and that the container 14, cover 16 and slide retainer 18 be constructed of a material inert with respect to the reagent and not interfere with any staining reaction between the reagent and the specimen being stained. However, since many of the staining techniques are similar to ELISA methodology, it is highly preferred to employ a material having low protein adsorbtivity such as, for example, styrene acrylonitrile.

While the invention has been described in connection with a slide retainer utilizing spring arms to clamp the slide edges in the guide channels, it will be understood that such spring arms are subject to wear. The spring arms 52 of the slide retainer 36 described in connection with FIG'S 1-5 are suitable for approximately ten to twenty insertions of slides before the spring arms normally begin to lose resiliency and their ability to retain the slides in the channels. Therefore, in another embodiment of the invention, a slide retainer is presented which has increased endurance and in addition has a simplified construction.

Referring to FIG'S 6 and 7, where like reference numbers denote like parts having like functions, there is illustrated a slide retainer consisting of an open cylindrical body 36 having one edge thereof adapted for mounting over the mouth 24 of the container 14 by means of the flange 38. In this embodiment openings are provided in the flange which correspond to the position of the projections 30 on the base surface 28 of the container 14. The openings 56 function in the same manner as the cutout portions 42 previously described to properly position the slide retainer 18 over the mouth 24 of the container. Members 46 are positioned on opposite interior wall surfaces of the cylindrical 36 and define opposed channels 44 in the facing surfaces thereof. The alignment and function of the channels 44 have already been described above in connection with the slide retainer of FIG'S 1-5.

Resilient, spring like clamping plates 58 extend between the channels 44 and are affixed to a side wall of each respective channel and thus serve to divide the interior of the cylindrical body 36 between the channels 44 into slide receiving areas 60. A wedge-shaped camming body 62 is affixed to a face of each of the clamping plates 58 and as illustrated the camming body is positioned so that the narrowest portion of the wedge is toward the bottom opening of the cylindrical body 36. In this embodiment, the slide edges are designed to be received in the channels 44 through the bottom of the cylindrical body 36 and the end portions of the slide pairs cat against the camming body 62 to create a slight bending distortion in the clamping plate 58 which causes it to act against the slides inserted therein, clamping the slides between the camming body 62 and a side wall of the channels 44 in which the slide pair is received. In the embodiments of the invention heretofore described, the container is provided with a liquid tight seal for shipping purposes which, once broken, is not restored. Under certain circumstances, however, it may be highly desirable to provide a liquid tight seal during a staining procedure or for storing a volatile reagent.

Figure 9:
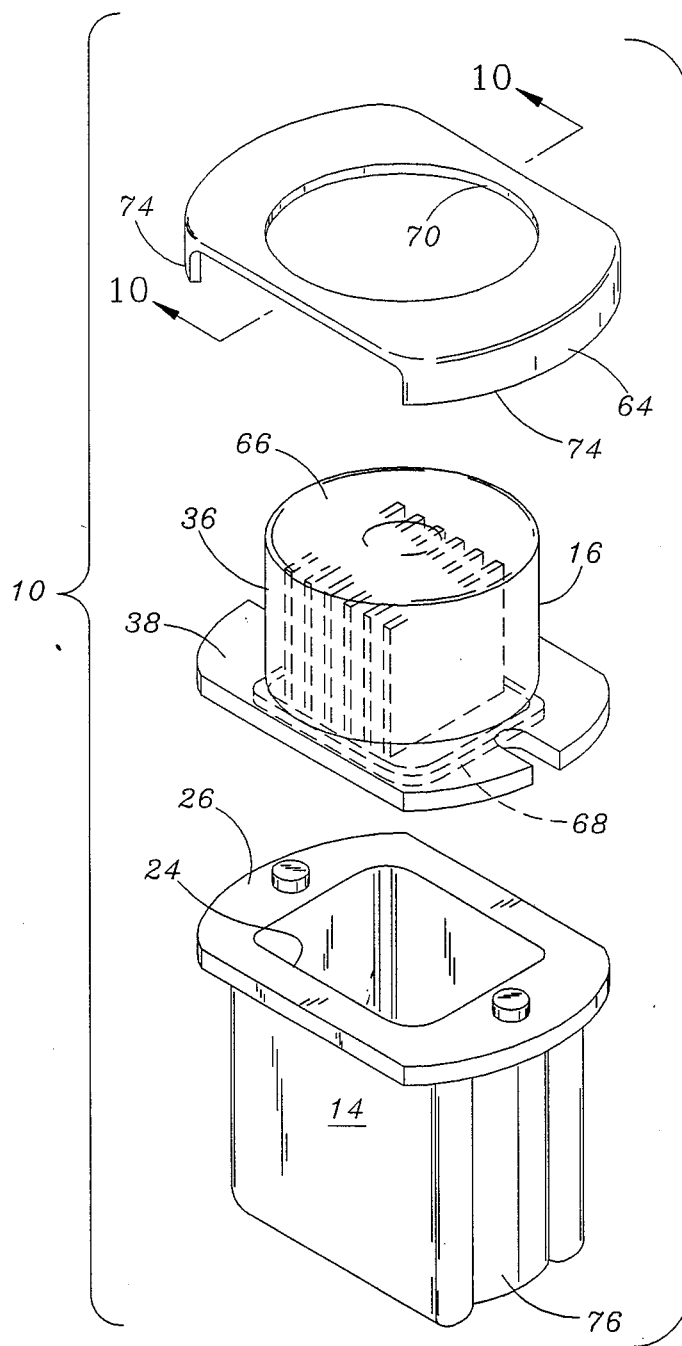
FIG. 9 is an exploded prospective view of another embodiment of the cassette of the present invention illustrating a slide retainer which also serves as the cover and having means for locking the slide retainer on the container.
Figure 10:
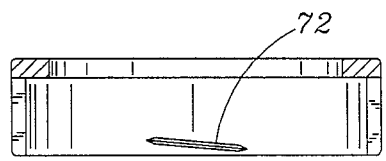
FIG. 10 is a side sectional view of a collar for locking the slide retainer on the container, taken along line 10—10 of FIG. 9.
Figure 11:
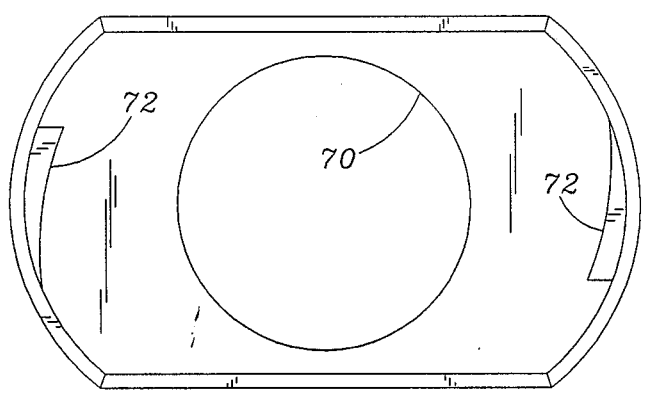
FIG. 11 is a bottom plan view of the collar of FIG. 10.

As illustrated in FIGS. 9, 10 and 11, in which like reference numbers denote like parts, a resealable embodiment of the invention is illustrated which comprises the container 14, the slide retainer 16 and additionally, a locking collar 64 which serves in the manner to be described hereinafter, to mechanically lock the slide retainer 16 in a sealing position over the mouth 24 of the container 14. As illustrated, the slide retainer 16 differs from the embodiments previously described in that the cylindrical body is closed at its upper end 66 and a downwardly extending sealing ring 68 is provided on its bottom surface. The sealing ring 68 is configured to match the configuration of the open mouth 24 of the container and is sized to provide a snug fit within the mouth when the slide retainer is in the sealing position. The locking collar 64, which corresponds in plan to the configuration of the container flange 26 and the closure flange 38, has a central opening 70 through which extends the cylindrical body 36 of the slide retainer 16 when the collar 64 is positioned on the upper surface of the flange 38 of the slide retainer 16. In the embodiment illustrated the plan configuration is elliptical and the ends of the locking collar 66 at the narrow dimensions are turned downwardly at 74 to receive the edges of the flange 26 on the container 14 and the flange 38 of the slide retainer 18. An interrupted helical thread 72 is formed on opposed facing surfaces defined by the downwardly turned end portions 74. The helical threads 72 act against the undersurface of the container flange 26 to pull the locking collar 64 down to clamp the closure 16 on the container 14 responsive to clockwise turning of the locking collar.

From the foregoing it will be apparent that the cassette of the present invention serves both as a container for tissue staining agent and as apparatus for carrying out staining of tissue samples. The cassette provides simple and economical apparatus for batch staining and handling a number of tissue slides with attendant improvement in the number of specimens which can be processed reproducibly by a single operator. At the same time, however, specificity and sensitivity are not sacrificed and, in fact, uniformity and reproduceability of specimen staining is actually enhanced by the batch staining process. Incubation times are not increased and in many cases can be shortened since the reagent as supplied in the kit of the present invention is somewhat more concentrated which permits a reduction in incubation time. Batch processing using the cassette of the present invention also provides increased efficiency in reagent use over the drop techniques currently employed by those in the field. For example, utilizing a number of different reagents, including many various primary and secondary (labelled and unlabelled) antibodies as well as ancillary reagents (PAP, APAAP, LAB, ABC), no adverse effect, as judged by the intensity and quality of staining, was determined when over 50 specimens/11 ml. of reagent were processed using cassettes of the invention. Also, no observable cross contamination of reagents occurred as a result of the transfer of batches of slides between reagents.

Various preferred embodiments and modifications of the invention have been described in the foregoing description and illustrated in the drawings. However, arrangements other than those described in detail in the specification, will occur to those persons skilled in the art, which arrangements lie within the spirit and scope of the invention. It will be understood, therefore, that minor changes may be made in the details of construction as well as in the combination and arrangement of parts without departing from the spirit and scope of the invention which should be limited only by the claims rendered hereto.

Having described the invention, I claim:

1. A cassette for tissue staining, said cassette comprising:
   a. a container having an interior for tissue staining reagent and including an open mouth;
   b. a slide retainer adapted to fit over the open mouth of said container for vertically suspending a plurality of specimen slides in said container interior, said slide retainer comprising a retainer body defining sidewalls and top and bottom ends, at least said bottom end being open for communication therethrough with said container interior, pairs of spacing means carried by opposing sidewalls of said retainer body for receiving the ends and upper edge portions of said specimen slides and for maintaining specimen containing surfaces of said specimen slides in spaced relationship with respect to adjacent surfaces, spring means associated with each of said pairs of spacing means, for acting against a surface of a slide and cooperating with said associated spacing means for holding said slide end portions in said retainer body; and c. means for supporting said retainer body over said open mouth of said container.

2. The cassette of claim 1 wherein said retainer body comprises an open ended cylinder in the lower edge of which is extended radially outwardly to define a flange for supporting said slide retainer over said container mouth.

3. The cassette of claim 1 wherein said pairs of spacing means comprise spaced apart vertical channels on opposite sidewalls of said retainer body, each said channel being open at its bottom and facing aspects and aligned with a corresponding channel on an opposite sidewall for receiving the edges of specimen slides to maintain the specimen containing surfaces of said slides in spaced relationship with respect to adjacent surfaces.

4. The cassette of claim 3 further including a depending resilient arm corresponding to each of said channels, each said resilient arm having at least the depending end thereof disposed in its respective channel, said arms being affixed at their upper ends to said retainer body and the depending ends thereof in said respective channels being free.

5. The cassette of claim 4 wherein said retainer body further includes an annular insert having a center opening which is configured to correspond to the configuration of said mouth of said container, a plurality of spaced apart inwardly extending fingers corresponding to said depending arms being affixed to opposing wall surfaces of said insert adjacent said opening thereof for carrying said depending arms.

6. The cassette of claim 3 further including spaced apart resilient wall members extending between corresponding channels on opposite sidewalls of said retainer body to define slide retainer spaces therebetween for receiving and securing end portions of said slides, a wedge-shaped camming body being affixed to a face of each of said resilient wall members for extension into each said slide receiving area, said wedge shaped body being positioned so that the narrowest portion of the wedge is disposed toward the container interior whereby the end portion of a slide inserted in said slide receiving area acts against the camming body to create a slight bending displacement of said wall member causing it to urge said camming body against said slide inserted therein to clamp the slides in said slide receiving area between said camming body and a side wall of said channel.

7. The cassette of claim 1 wherein said top end of said retainer body is closed and locking means are provided to secure said retainer body over said mouth of said container whereby said retainer body serves as a closure for said container.

8. The cassette of claim 7 wherein said container includes a flange adjacent said open mouth and said container is provided with a corresponding flange about the edge of said depending skirt, said locking means comprising a locking collar having an essentially planer undersurface corresponding in plan to said container flange on said closure flange, said locking collar having a centrally located opening through which extends said retainer body when said collar is positioned on the upper surface of said closure flange, portions of two opposite edges of said collar extending downwardly to define opposed faces which cooperate with said planer undersurface to receive and overlie said container flange and said closure flange, an inclined thread formed on each of said faces for removable locking of said closure on said container.

9. The cassette of claim 1 wherein at least a portion of a wall of said container is adapted for magnified viewing of the interior of said container.

* * * * *